United States Patent
Lafyatis et al.

(10) Patent No.: US 9,815,049 B2
(45) Date of Patent: Nov. 14, 2017

(54) SELECTIVITY OF IONIC LIQUID ALKYLATION

(71) Applicant: UOP LLC, Des Plaines, IL (US)

(72) Inventors: David S. Lafyatis, Schaumburg, IL (US); Sean G. Mueller, Des Plaines, IL (US); Zhanping Xu, Inverness, IL (US); Douglas A. Nafis, Mount Prospect, IL (US); Robert Mehlberg, Wheaton, IL (US); Kurt Detrick, Glen Ellyn, IL (US); Avram M. Buchbinder, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/331,702

(22) Filed: Oct. 21, 2016

(65) Prior Publication Data

US 2017/0144141 A1    May 25, 2017

Related U.S. Application Data

(60) Provisional application No. 62/253,316, filed on Nov. 10, 2015.

(51) Int. Cl.
| | |
|---|---|
| C07C 2/72 | (2006.01) |
| B01J 31/02 | (2006.01) |
| C07C 6/04 | (2006.01) |
| C07C 5/27 | (2006.01) |
| C07C 2/58 | (2006.01) |
| C07C 2/26 | (2006.01) |

(52) U.S. Cl.
CPC ....... *B01J 31/0282* (2013.01); *B01J 31/0279* (2013.01); *B01J 31/0284* (2013.01); *B01J 31/0288* (2013.01); *C07C 2/26* (2013.01); *C07C 2/58* (2013.01); *C07C 5/2727* (2013.01); *C07C 6/04* (2013.01); *B01J 2231/20* (2013.01); *B01J 2231/44* (2013.01); *B01J 2231/52* (2013.01); *B01J 2231/543* (2013.01)

(58) Field of Classification Search
CPC ....................................................... C07C 2/72
USPC ................................................ 585/716, 722
See application file for complete search history.

(56) References Cited

U.S. PATENT DOCUMENTS

| | | |
|---|---|---|
| 8,067,656 B2 | 11/2011 | Luo et al. |
| 8,198,499 B2 | 6/2012 | Luo et al. |
| 8,198,500 B2 | 6/2012 | Elomari et al. |
| 2014/0128654 A1 | 5/2014 | Fang et al. |

OTHER PUBLICATIONS

Schilder et al., "Effective and intrinsic kinetics of liquid-phase isobutane/2-butene alkylation catalyzed by chloroaluminate ionic liquids", Industrial and Engineering Chemistry Research, (2013), v 52, n 5, p. 1877-1885.

Aschauer et al., "Liquid-phase isobutane/butene-alkylation using promoted Lewis-acidic IL-catalysts", Catalysis Letters, (2011), v 141, n 10, p. 1405-1419.

*Primary Examiner* — Thuan D Dang

(57) ABSTRACT

A method of controlling a hydrocarbon conversion process is described. The method involves introducing a reactant into a reaction zone containing an ionic liquid catalyst. The reaction zone has at least two zones. The mass transfer resistance in the second zone is greater than the mass transfer resistance in the first zone.

14 Claims, 4 Drawing Sheets

SELECTIVITY OF IONIC LIQUID ALKYLATION

CROSS-REFERENCE TO RELATED APPLICATION

This application claims priority from Provisional Application No. 62/253,316 filed Nov. 10, 2015, the contents of which are hereby incorporated by reference

BACKGROUND OF THE INVENTION

Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. ethylbenzene, cumene, dodecylbenzene, etc.).

The alkylation of paraffins with olefins for the production of alkylate for gasoline can use a variety of catalysts. The choice of catalyst depends on the end product a producer desires. Typical alkylation catalysts include concentrated sulfuric acid or hydrofluoric acid. However, sulfuric acid and hydrofluoric acid are hazardous and corrosive, and their use in industrial processes requires a variety of environmental controls.

Solid catalysts are also used for alkylation. However, solid catalysts are generally rapidly deactivated and may be prohibitively expensive.

Acidic ionic liquids have been used as an alternative to the commonly used strong acid catalysts in alkylation processes. Ionic liquids are essentially salts in a liquid state, and are described in U.S. Pat. Nos. 4,764,440, 5,104,840, and 5,824,832. The properties vary extensively for different ionic liquids, and the use of ionic liquids depends on the properties of a given ionic liquid. Depending on the organic cation of the ionic liquid and the anion, the ionic liquid can have very different properties. The most common ionic liquid catalyst precursors for alkylation include imidazolium or pyridinium-based cations coupled with the chloroaluminate anion ($Al_2Cl_7^-$).

Ionic liquids provide advantages over other liquid catalysts, including being non-volatile.

Other hydrocarbon conversion processes, including isomerization, oligomerization, disproportionation, and reverse disproportionation, also use ionic liquid catalysts.

The hydrocarbon conversion reaction will proceed simply by contacting the hydrocarbon feed and the ionic liquid catalyst. The reaction is biphasic and takes place at the interface in the liquid state due to the low solubility of hydrocarbons in ionic liquids. The hydrocarbon feed and the ionic liquid catalyst are often mixed to produce smaller ionic liquid catalyst droplets and thereby increase the mass transfer resulting in an increased reaction rate.

However, there is a need to control the mass transfer resistance in the reactor to control the reaction product.

SUMMARY OF THE INVENTION

One aspect of the present invention is a method of controlling a hydrocarbon conversion process. In one embodiment, the method involves introducing a reactant into a reaction zone containing an ionic liquid catalyst comprising ionic liquid droplets, the reaction zone having at least two zones, the first zone having a first mass transfer resistance in the ionic liquid droplets and the second zone having a second mass transfer resistance in the ionic liquid droplets greater than the first mass transfer resistance.

DETAILED DESCRIPTION OF THE INVENTION

Figure 1:
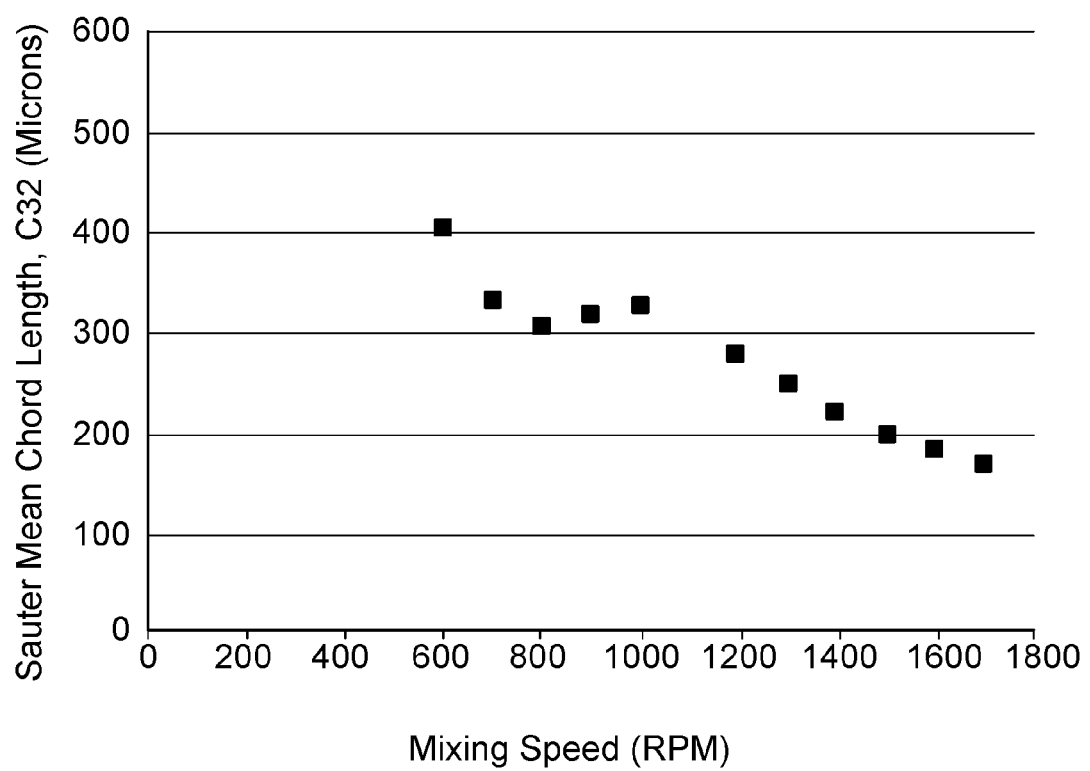
FIG. 1 is a graph showing the effect of mixing speed on the Sauter mean chord length of the ionic liquid droplets.

The present invention involves the use of ionic liquids as catalysts for hydrocarbon conversion processes, including, but not limited to, alkylation, oligomerization, isomerization, disproportionation, and reverse disproportionation. In hydrocarbon conversion processes using ionic liquid catalysts, the continuous phase is typically the hydrocarbon phase and the ionic liquid catalyst is the dis-continuous phase.

For ease of discussion, the process will be described for alkylation reactions, and more particularly, the reaction of isobutane with butene to make $C_8$ alkylate as the desired product. The reaction is typically performed at conditions of complete butene conversion. As the product alkylate concentration builds up down the length of a reaction zone, there are undesired secondary reactions, for example the reaction of the product alkylate with butene. This secondary reaction leads to heavy products which may not be within the desired boiling point range. It may also eventually lead to very large molecules which may become conjunct polymer and deactivate the ionic liquid catalyst. Another undesired secondary reaction is the isomerization of trimethylpentanes to dimethylhexanes which gives rise to a product having lower octane number. Thus, it is desirable to minimize secondary reactions.

One way to minimize the undesirable secondary reaction is to increase the mass transfer resistance at downstream locations in the reaction zone. In a reaction zone having a single reactor with two or more zones, the increased mass transfer resistance occurs in the second (or later) zone. In a reaction zone with more than one reactor where each reactor comprises a zone (or more than one zone), the increased mass transfer resistance takes place in the second (or later) reactor.

Although not wishing to be bound by theory, it is believed that some of the effects described below involve internal mass transfer resistance, others involve external mass transfer resistance, and some may involve both. The term mass transfer resistance is intended to cover all of these.

When the mass transfer resistance is increased down the length of the reactor (or is increased in later reactors), the access of the olefin to the reaction site is reduced, as well as the access of the desired product alkylate material to the reaction site, which reduces the likelihood of producing heavier end molecules. This should lead to a more desirable product distribution and a reduction in the amount of conjunct polymer produced.

Thus, in a reaction sequence of:

$$A+B \rightarrow C$$

$$B+C \rightarrow D$$

where A is isobutane, B is butene, C is the desired alkylate, and D is the undesirable heavy product, the increased mass transfer resistance is relied on to restrict the access of B and C to the catalyst.

When mass transfer resistance is increased down the length of the reactor (or is increased in later reactors), the access of one of the desired primary products (trimethylpentanes) to the reaction site is reduced, which reduces the likelihood of isomerization to less desired dimethylhexanes. This should lead to a more desirable product distribution and alkylate of higher octane.

Thus, in a reaction sequence of:

$$A+B \rightarrow C$$

$$C \rightarrow C'$$

where C is a more desired $C_8$ isomer such as a trimethylpentane and C' is a less desired $C_8$ isomer such as a dimethylhexane, the increased mass transfer resistance is relied on to restrict the access of C to the catalyst.

The mass transfer resistance of either the first zone or the second zone can be changed, or the mass transfer resistance of both the first and second zones can be changed.

The mass transfer resistance for reaction in an ionic liquid droplet can be controlled in several ways. One method involves controlling the size of the ionic liquid droplets. Larger droplets lead to longer mass transfer lengths and therefore increased mass transfer resistance. The droplet size can be controlled by the amount of shear that is imparted to the ionic liquid/hydrocarbon mixture.

In some embodiments, the mass transfer resistance of the first and/or second zone is changed by changing the size of the droplets in the two (or more) zones. For example, the droplets in the first zone can be smaller than the droplets in the second zone. One method of accomplishing this is to increase the shear rate of the first zone, or decrease the shear rate of the second zone, or both. For example, methods to change the shear rate in a stirred tank reactor include changing the impeller speed, changing the impeller design, or both.

Another method of changing the size of droplets in the first and/or second zone is to change the design of a static mixer positioned before the zone. According to the Handbook of Industrial Mixing: Science and Practice, Ed. Paul et al., ©2004 by John Wiley & Sons Inc., the droplet size for static mixers is a function of the physical properties of the fluid (dispersed phase viscosity, dispersed phase density, continuous phase density, and interfacial tension), the geometrical characteristics of the static mixer, and the energy dissipation imparted, which is itself a function of the pressure drop, static mixer length, fluid velocity and density.

Thus, there are various ways to change the droplet size: for example, changing the velocity of the fluid, changing the length of the static mixer (i.e. more/less elements), and changing the static mixer element type are all ways to change the droplet size without changing the fluid properties.

Likewise, for stirred tanks the droplet size is a function of the tank/impeller geometry, the physical properties of the fluids (dispersed phase viscosity, dispersed phase density, continuous phase density, and interfacial tension), and the energy dissipation, which itself is a function of the impeller rotational speed, tank/impeller geometries, and fluid properties.

Thus, droplet size can be changed in a stirred tank by changing the tank and/or impeller geometry and by changing the impeller rotational speed.

FIG. 1 is a graph showing the effect of mixing speed on the Sauter mean chord length of ionic liquid droplets for a pitched blade turbine at an ionic liquid volume fraction of 0.1. The Sauter mean chord length decreases in close to a linear fashion above 1000 rpm. Below 1000 rpm, it is believed that the mixing was not homogeneous. The Sauter mean chord length can be determined using the Sauter mean definition $(x_{32} = \Sigma(x_i^3 * f_i)/\Sigma(x_i^2 * f_i))$, which can be applied to chord length as well as diameter.

The droplet size can also be changed by increasing the amount of ionic liquid in the second zone. As the volume fraction of the dispersed phase is increased, the size of the droplets has generally been found to increase. The overall surface area of the ionic liquid catalyst droplet in the reactor is also increased, which results in increased mass transfer resistance because the reactants are depleted faster.

Moreover, increasing the size of the droplets in the second zone has the additional benefit of making the post reaction zone separation of the ionic liquid from the alkylate product (and other hydrocarbons) easier, improving the economics of alkylation process.

Another method of changing the mass transfer resistance of the first zone, the second zone, or both, involves controlling the viscosity of the ionic liquid under the reactor operating conditions. By the "viscosity of the ionic liquid under the reactor operating conditions" we mean the viscosity of the ionic liquid under the conditions of use in the reactor. For example, if the same ionic liquid is used in both zones, but the temperature of the second zone is lower, the viscosity of the ionic liquid under the reactor operating conditions of the first zone will be less than the viscosity of the ionic liquid under the reactor operating conditions of the second zone.

Increasing the viscosity of the ionic liquid under the reactor operating conditions leads to increased mass transfer resistance by reducing the bulk diffusivity of the hydrocarbons in the ionic liquid. The viscosity of an ionic liquid may be adjusted by changing the temperature, changing the ionic liquid, or through the use of additives.

The viscosity of the ionic liquid catalyst under the reactor operating conditions in the first zone, the second zone, or both can be changed.

The viscosity of the ionic liquid under the reactor operating conditions in the second zone is greater than the viscosity of the ionic liquid under the reactor operating conditions in the first zone.

In some embodiments, the viscosity of the ionic liquid under the reactor operating conditions is changed by operating the first zone at a higher temperature than the second zone while using the same ionic liquid in both zones. This can be accomplished by increasing the temperature in the first zone, decreasing the temperature in the second zone, or both. Table 1 provides the viscosity for a variety of ionic liquids at different temperatures. By proper selection of the operating temperature of the first and second zones (or more), the viscosity of the ionic liquid under the reactor operating conditions in the various zones can be changed.

TABLE 1

| Ionic liquid | Temperature (° C.) | Viscosity (cSt) |
|---|---|---|
| Tri-butyl-hexyl-phosphonium Bromohexachlorodialuminate (TBHP-Al$_2$BrCl$_6$) | 23 50 70 | 173.7 53.5 27.2 |
| Tri-butyl-pentyl-phosphonium Chloroaluminate (TBPP-Al$_2$Cl$_7$) | 25 50 70 | 86.2 31.86 17.4 |
| Tri-butyl-pentyl-phosphonium Bromohexaclorodialuminate (TBPP-Al$_2$BrCl$_6$) | 23 50 70 | 112.1 37.07 19.98 |
| Tri-butyl-hexyl-phosphonium Chloroaluminate (TBHP-Al$_2$Cl$_7$) | 23 50 70 | 69.79 25.3 14.3 |
| 1-butyl-3-methylimidazolium Chloroaluminate (BMIM-Al$_2$Cl$_7$) | 23 50 70 | 14.95 7.79 5.6 |
| n-butyl-pyridinium Chloroaluminate (BPy-Al$_2$Cl$_7$) | 23 50 70 | 21.54 8.79 6 |
| 1-octyl-3-methylimidazolium Chloroaluminate (OMIM-Al$_2$Cl$_7$) | 23 50 70 | 27.28 12.83 8 |
| Hexadecyl-pyridinium Chloroaluminate (HDPy-Al$_2$Cl$_7$) | 23 50 70 | 119.8 41.83 22.95 |
| Tri-butyl-hexyl-phosphonium Chloroaluminate (TBHP-Al$_2$Cl$_7$) | 25 50 70 | 111.1 39.14 22.02 |
| Tri-butyl-methyl-phosphonium Chloroaluminate (TBMP-Al$_2$Cl$_7$) | 25 50 70 | 55.41 22.34 12.74 |
| Tri-ethyl-ammonium Chloroaluminate (Et$_3$NH—Al$_2$Cl$_7$) | 25 50 70 | 16.36 8.32 5.56 |
| Tri-ethyl-ammonium chloroaluminate with copper chloride (Et$_3$NH—Al$_2$Cl$_7$ + 0.19 mol CuCl) | 25 50 70 | 18.43 9.279 6.092 |

In other embodiments, the viscosity of the ionic liquid under the reactor operating conditions is changed by using an ionic liquid in the second zone which has a higher viscosity than the ionic liquid used in the first zone.

For example, Table 1 provides the viscosity of several ionic liquids. By proper selection of the ionic liquids in the different zones, the viscosity of the ionic liquid under the reactor operating conditions can be changed.

In still other embodiments, the viscosity of the ionic liquid under the reactor operating conditions is changed by adding a viscosity reducing additive to the ionic liquid catalyst in the first zone, adding a viscosity increasing additive to the ionic liquid in the second zone, or both. Non-ionic compounds, including by not limited to, dichloromethane and bromobenzene may be used to reduce the viscosity of an ion liquid. A variety of viscosity modifiers are described in U.S. application Ser. No. 14/568,698, entitled VISCOSITY MODIFIERS FOR DECREASING THE VISCOSITY OF IONIC LIQUIDS, filed Dec. 12, 2014, which is incorporated herein by reference. The viscosity can also be changed by adding a second ionic liquid with a higher or lower viscosity to the ionic liquid catalyst.

When different ionic liquids are used in the two zones or when additives are included, the ionic liquid from the first zone would need to be separated from the alkylate (and unreacted paraffin) before the second zone to keep the different ionic liquids separated. Known separation techniques could be used, including but not limited to, one or more of a gravity separation zone, a coalescer zone, a filtration zone, an adsorption zone, a scrubbing zone, an electrostatic separation zone, an absorption zone, an extraction zone, a distillation zone, or combination thereof. Combinations of these approaches could also be used.

For ease of discussion, the process was described with a reaction zone including one reactor with two zones and a reaction zone including two reactors each with one zone. However, those of skill in the art will understand that it is not limited to those arrangements.

The reaction zone has at least two zones. The mass transfer resistance in the first zone is less than the mass transfer resistance in the last zone. In some embodiments, the reaction zone can comprise one reactor with two, three, four (or more) zones. Alternatively, the reaction zone can comprise two or more reactors with each reactor having one or more zones. For example, the reaction zone can comprise two reactors, the first reactor being the first zone and the second reactor being the second zone. In another embodiment, the reaction zone can comprise two reactors with both reactors including two zones for a total of four zones. In another embodiment, the reaction zone can comprise three reactors with one reactor have one zone, one reactor having two zones, and the third reactor having three for a total of six zones. Other combinations of the number of reactors and the number of zones in each reactor could be used, as would be understood by those of skill in the art. In some embodiments, the reaction zones comprise one or more continuous stirred tank reactors (CSTR) or one or more plug flow reactors (PFR), for example. Other reactor types could also be utilized to achieve the same effect.

In a series of CSTR's, the change in mass flow resistance could be accomplished in a variety of ways. For example, the stirring rates in the later reactors in the series could be reduced, the design of static mixers through which ionic liquid is introduced to the reactors could be altered, a lower temperature could be used in the later reactors, higher ionic liquid volume fraction could be used in later reactors, a more viscous ionic liquid could be used in the later reactors, a viscosity reducing additive could be used in the earlier reactors, a viscosity increasing additive could be used in the later reactors, or the amount of conjunct polymer in the later reactors could be increased.

The same principles could be applied to PFR reactor systems or any other reactor types.

Figure 2:
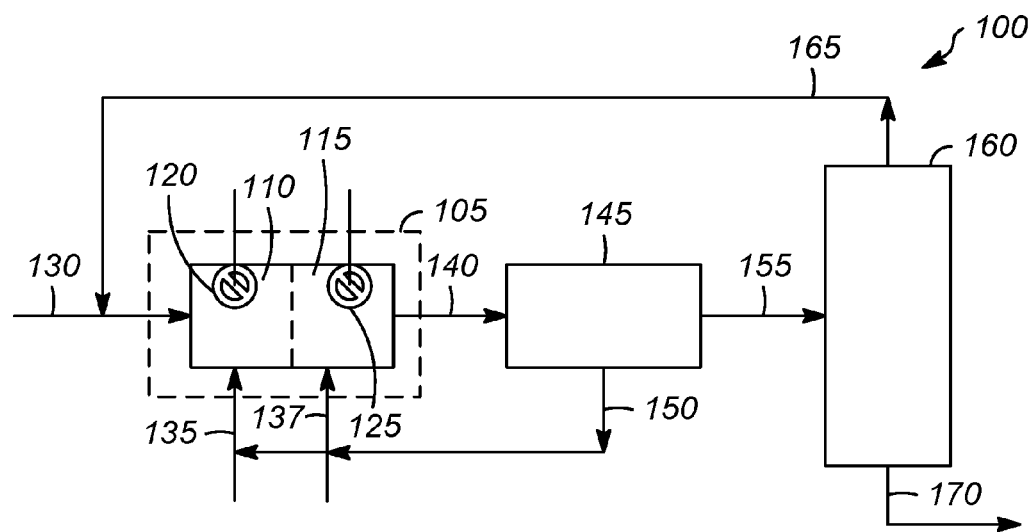
FIG. 2 illustrates one embodiment of an alkylation process according to the present invention.

One embodiment of a process 100 according to the present invention is illustrated in FIG. 2. For the purposes of the following discussion, butene and isobutane will be used as the main reactants, with the understanding that many other paraffin and olefins may be utilized in a similar manner.

Reaction zone 105 comprises a single reactor with first and second zones 110 and 115. The first zone 110 has an ionic liquid droplet size controller 120, and the second zone 115 has an ionic liquid droplet size controller 125. The ionic liquid droplet size controllers 120, 125 could be one or more of mixers operated at different shear rates, mixers having different designs, and ionic liquid inlet controllers for adding ionic liquid catalyst so that the amount of ionic liquid catalyst in the second zone 115 is greater than the amount of ionic liquid catalyst in the first zone 110. If the ionic liquid droplet size controllers 120, 125 include a mixer, the mixer may be an impeller, a static mixer or another type of mixing device as would be known by one skilled in the art.

The hydrocarbon feed stream 130 containing isoparaffin, such as isobutane, and olefin, such as butene, and an ionic liquid catalyst stream 135 are sent to the first zone 110.

The isobutane reacts with the butene in the presence of the ionic liquid catalyst to form the C$_8$ alkylate. The reaction mixture from the first zone 110, which contains C$_8$ alkylate, unreacted isobutane, unreacted butene, and ionic liquid catalyst, flows into the second zone 115. In some embodiments, a second ionic liquid catalyst stream 137 is introduced into the second zone 115 to increase the amount of ionic liquid catalyst in the second zone 115. In some embodiments (not shown) butene can be added to the second zone, if desired.

The ionic liquid droplet size controller 125 in the second zone 115 may provide ionic liquid catalyst droplets having a larger size than the ionic liquid catalyst droplets in the first zone 110. The droplet size can be increased by one or more of adding ionic liquid to later zones and decreasing the mixing intensity in later zones (e.g., by changing the mixer design or speed). Adding ionic liquid to the second zone 115 (and/or later zone(s)) increases the phase fraction of ionic liquid catalyst in the later zones and thus increases the coalescence rate of droplets in the reactor. Decreasing the mixing intensity in the second zone 115 (and/or subsequent zones) reduces the shear field in the second zone 115 and thus decreases the breakage rate of droplets in the second zone 115 compared to the first zone 110. The mixing intensity can be varied using a motor-control system to vary the speed on the impellers at optimal conditions for increasing the ionic liquid droplet size in the second zone 115 and/or by changing the mixer design.

The increased size of the ionic liquid catalyst droplets in the second zone 115 results in increased mass transfer resistance and thus reduced reactivity. As a result, less alkylate product reacts with butene or alkylate product to form larger molecules than would be the case if the droplet size in both zones were the same. The larger droplets in the second zone 115 also aid in recovering the ionic liquid catalyst in the ionic liquid separation zone 145.

The effluent 140 from the second zone 115 includes alkylate, unreacted isobutane, possibly minor amounts of unreacted butene, and ionic liquid catalyst. The effluent 140 is sent to an ionic liquid separation zone 145 where it is separated into an ionic liquid phase and a hydrocarbon phase. The hydrocarbon phase includes the $C_8$ alkylate, unreacted isobutane, and any unreacted butene. Any suitable separation zone 145 can be used. Examples of separation zones include, but are not limited to, one or more of a gravity separation zone, a coalescer zone, a filtration zone, an adsorption zone, a scrubbing zone, an electrostatic separation zone, an absorption zone, an extraction zone, a distillation zone, or combination thereof.

The ionic liquid phase exits the ionic liquid separation zone 145 as ionic liquid stream 150. Ionic liquid stream 150 can be combined with ionic liquid catalyst stream 135 and recycled to the first zone 105 and/or the second ionic liquid catalyst stream 137 and recycled to the second zone 115. The ionic liquid can be regenerated (not shown) if needed before being recycled.

The hydrocarbon phase exits the ionic liquid separation zone 145 as hydrocarbon stream 155. Hydrocarbon stream 155 contains the alkylate, unreacted isobutane, and any unreacted butene. The hydrocarbon stream 155 is sent to a hydrocarbon separation zone 160 where it is separated into an isoparaffin recycle stream 165 and an alkylate stream 170.

Hydrocarbon separation zone 160 can be any suitable separation zone, including, but not limited to, one or more fractionation columns, stripping columns, flashing, selective adsorption, or combinations thereof.

The isoparaffin recycle stream 165 can be combined with the hydrocarbon feed stream 130 or introduced directly into the first zone.

The alkylate stream 170 can be recovered.

Figure 3:
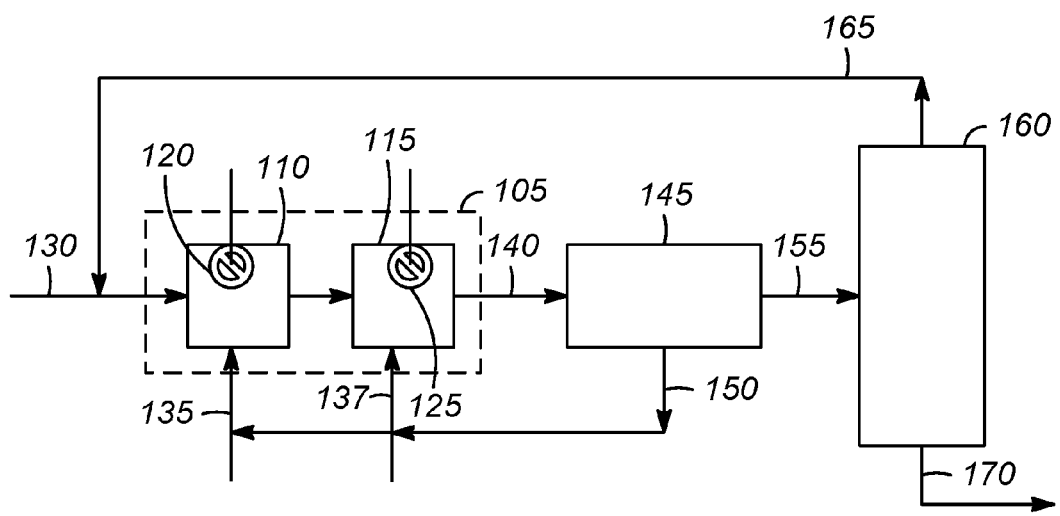
FIG. 3 illustrates another embodiment of an alkylation process according to the present invention.

FIG. 3 is similar to FIG. 2 except that the reaction zone 105 comprises separate reactors for the first and second zones 110, 115.

In some embodiments, butene is added to the second zone 115 (not shown).

Alternatively, rather than using ionic liquid droplets controllers in the first and zones 110, 115, the mass transfer resistance could be changed by changing the viscosity of the ionic liquid catalyst under the reactor operating conditions. One way this could be done is to use different temperatures in the first and second zone. The temperature in the second zone could be lowered (or the temperature in the first zone could be increased) to increase the relative mass transfer resistance in the second zone.

Another option to change the mass transfer resistance is to control the relative amount of ionic liquid catalyst in the first and second zones 110, 115. The amount of ionic liquid catalyst streams 135, 137 being introduced into the first and second zones 110, 115 could be controlled so that the amount of ionic liquid catalyst in the second zone 115 was greater than the amount of ionic liquid catalyst in the first zone 110.

The mass transfer resistance could also be controlled by controlling the amount of conjunct polymer in the first and second reaction zones 110, 115. The relative amounts of fresh ionic liquid, regenerated ionic liquid (in which conjunct polymer formed in the reaction has been removed), and spent ionic liquid (in which conjunct polymer has not been removed) added to the first and second zones 110, 115 can be used to control the viscosity in the first and second zones 110, 115. The amount of fresh ionic liquid catalyst or regenerated ionic liquid catalyst added to the first zone 110 could be increased to maintain a lower viscosity in the first zone 110. The amount of spent ionic liquid added to the second zone 115 could be increased in the second zone 115 to increase the viscosity in the second zone 115. Some recycled spent ionic liquid could be added to the first zone 110, and some fresh ionic liquid catalyst or regenerated ionic liquid catalyst could be added to the second zone 115, if desired. By controlling the amounts of fresh, regenerated, and recycled spent ionic liquid catalyst added to the first and second zones 110, 115, the viscosity of the ionic liquid catalyst in the first and second zones 110, 115 could be controlled so that viscosity in the second zone 115 is higher than the viscosity in the first zone 110.

Figure 4:
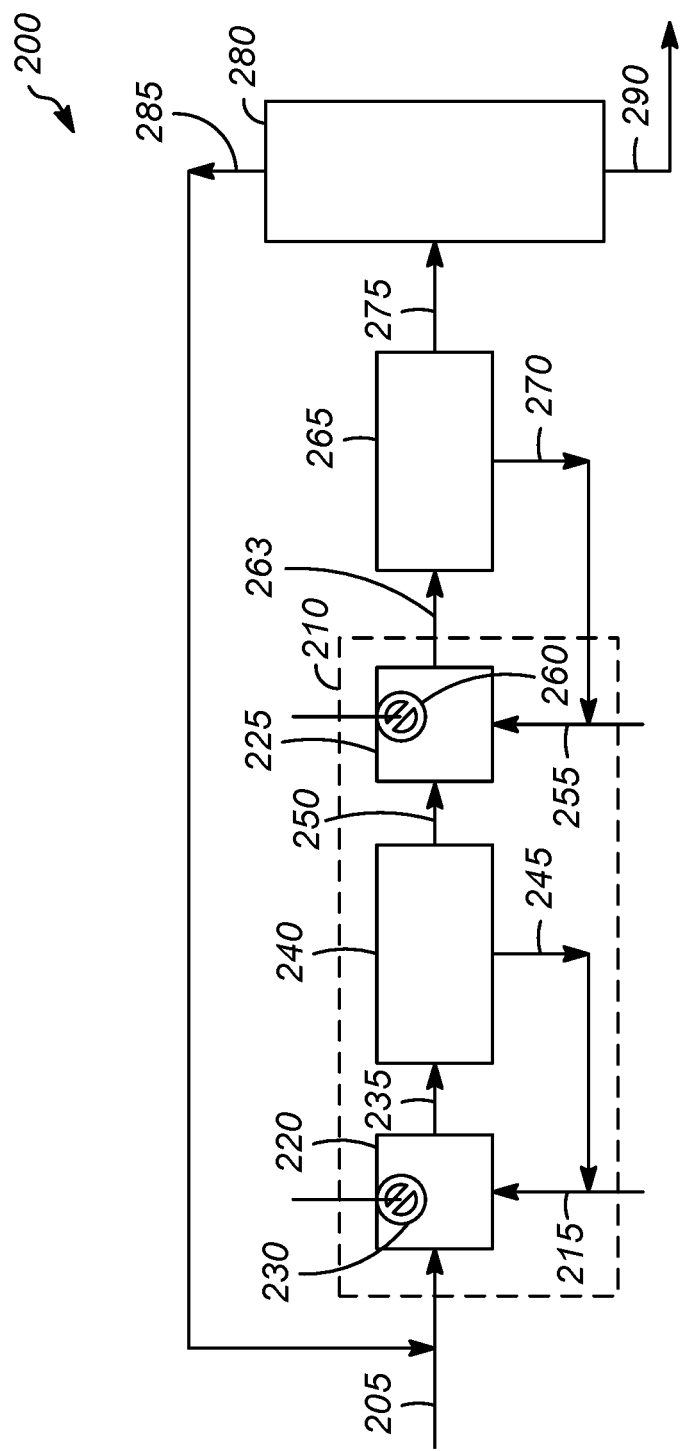
FIG. 4 illustrates another embodiment of an alkylation process according to the present invention.

FIG. 4 illustrates a process which could be used when the mass transfer resistance is changed by using different ionic liquids in the first and second zones or by using viscosity increasing or decreasing additives in the ionic liquid(s) in one or both zones.

In this embodiment, the hydrocarbon feed stream 205 is introduced into reaction zone 210 along with first ionic liquid catalyst stream 215. Hydrocarbon feed stream 205 includes isoparaffin and olefin. For the purposes of the following discussion, butene and isobutane will be used as the main reactants, with the understanding that many other paraffin and olefins may be utilized in a similar manner.

Reaction zone 210 includes first and second zones 220, 225. The first zone 220 can optionally include an ionic liquid droplet size controller 230, as discussed above.

The isobutane and butene in the hydrocarbon feed stream 205 react in the presence of the first ionic liquid catalyst stream 215 in the first zone 220 to form alkylate. The effluent 235 from the first zone 220 includes the first ionic liquid catalyst, alkylate, unreacted isobutane, and any unreacted butene.

Because the ionic liquid catalysts in the first and second zones 220, 225 are different, they should be kept separate. Consequently, a first ionic liquid separation zone 240 is included in the process, The effluent 235 is sent to the first ionic liquid separation zone 240 where the effluent is separated into a first ionic liquid catalyst phase and a hydrocarbon phase. The first ionic catalyst phase is removed from the first ionic liquid separation zone 240 as first ionic liquid stream 245. First ionic liquid stream 245 can be combined with first ionic liquid catalyst stream 215 and recycled to the first zone 220.

The hydrocarbon phase is removed from the first ionic liquid separation zone 240 as hydrocarbon stream 250, which includes $C_8$ alkylate, unreacted isobutane, and any unreacted butene. Hydrocarbon stream 250 is introduced into the second zone 225 along with second ionic liquid catalyst stream 255. The second zone 225 can optionally include an ionic liquid droplet size controller 260 as described above, if desired.

Because the viscosity of the second ionic liquid catalyst under the reactor operating conditions is lower than the viscosity of the first ionic liquid catalyst under the reactor operating conditions, less $C_8$ alkylate reacts with butene or $C_8$ alkylate to form larger molecules in the second zone 225 than would be the case if the droplet size in both zones were the same.

The effluent 263 from the second zone 225 includes alkylate, unreacted isobutane, any unreacted butene, and the second ionic liquid catalyst. The effluent 263 is sent to a second ionic liquid separation zone 265 where it is separated into an ionic liquid phase and a hydrocarbon phase. Any suitable ionic liquid separation zone can be used. The first and second ionic liquid separation zones 240, 265 can be the same or they can be different, if desired.

The ionic liquid phase exits the second ionic liquid separation zone 265 as second ionic liquid stream 270. Second ionic liquid stream 270 can be combined with second ionic liquid catalyst stream 255 and recycled to the second zone 225.

The hydrocarbon phase includes the alkylate, unreacted isobutane, and any unreacted butene. The hydrocarbon phase exits the second ionic liquid separation zone 265 as hydrocarbon stream 275 and is sent to a hydrocarbon separation zone 280 where it is separated into an isoparaffin recycle stream 285 and an alkylate stream 290. Any suitable hydrocarbon separation can be used, as discussed above.

The isoparaffin recycle stream 285 can be combined with the hydrocarbon feed stream 205 or introduced directly into the first zone 220.

The alkylate stream 290 can be recovered.

In some embodiments, the temperatures of the first and second zones 220, 225 are different.

In some embodiments, butene is added to the second zone 225 (not shown).

In some embodiments, the ionic liquid droplet size in zone 225 is different from the ionic liquid droplet size in zone 220.

The arrangement of FIG. 4 could be used to change the mass transfer resistance by adding a viscosity decreasing additive to the first zone 220, or by adding a viscosity increasing additive to the second zone 225, or both.

The arrangement of FIG. 4 could be used to change the mass transfer resistance by controlling the relative amount of ionic liquid catalyst in the first and second zones 220, 225. The amount of ionic liquid catalyst being introduced into the first and second zones 220, 225 could be controlled so that the amount of ionic liquid catalyst in the second zone 225 was greater than the amount of ionic liquid catalyst in the first zone 220.

The arrangement of FIG. 4 could also be used to change the mass transfer resistance by controlling the amount of conjunct polymer in the first and second reaction zones 220, 225.

The relative amounts of fresh, regenerated, and spent ionic liquid added to the first and second zones 220, 225 can be used to control the viscosity in the first and second zones 220, 225. The amount of fresh ionic liquid catalyst or regenerated ionic liquid catalyst added to the first zone 220 could be increased to maintain a lower viscosity in the first zone 220. The amount of spent ionic liquid added to the second zone 225 could be increased in the second zone 225 to increase the viscosity in the second zone 225. Some spent ionic liquid could be added to the first zone 220, and some fresh ionic liquid catalyst or regenerated ionic liquid catalyst could be added to the second zone 225, if desired. By controlling the amounts of fresh, regenerated, and spent ionic liquid catalyst added to and/or removed from the first and second zones 220, 225, the viscosity of the ionic liquid catalyst in the first and second zones 220, 225 could be controlled so that viscosity in the second zone 225 is higher than the viscosity in the first zone 220.

Figure 5:
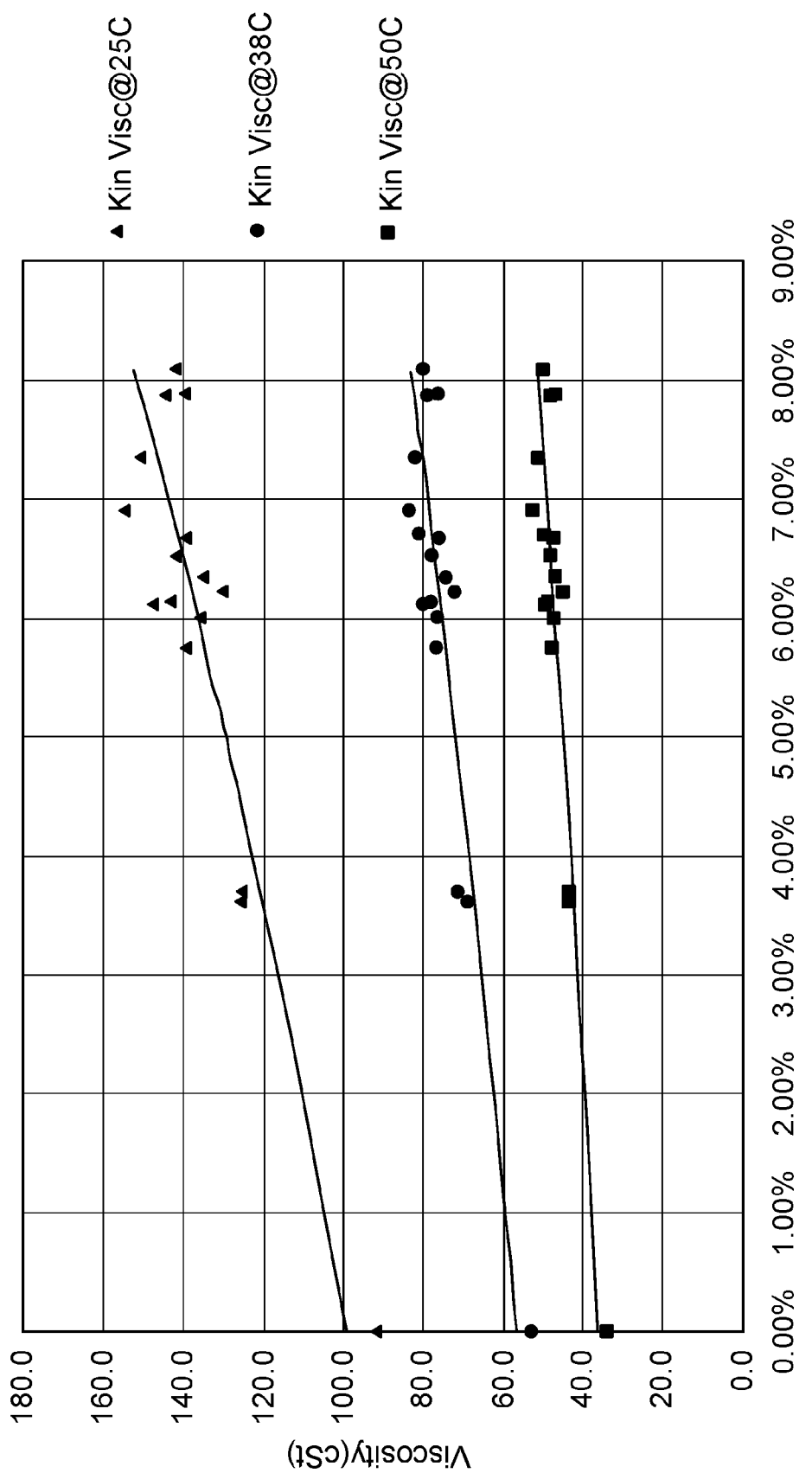
FIG. 5 is a graph showing the kinematic viscosity of an ionic liquid as a function of the amount of conjunct polymer at various temperatures.

In hydrocarbon conversion processes such as alkylation of isoparaffin with olefin, high molecular weight material known as conjunct polymer is generated and remains on the catalyst. As shown in WO 2015/148182, conjunct polymer results in increased ionic liquid viscosity. In a continuous pilot plant operation, isobutane, 2-butene, and hydrochloric acid were reacted in a continuously stirred tank reactor with ionic liquid catalyst. The reactor effluent was separated by gravity, and the ionic liquid catalyst was recycled to the reactor. Periodically, portions of the spent ionic liquid were removed from circulation, and fresh ionic liquid was added to circulation in order to control the amount of conjunct polymer present and the viscosity of the ionic liquid. The amount of conjunct polymer and the viscosity of the ionic liquid was determined according to the procedure in WO2015/148182 by analyzing portions of the spent ionic liquid after removing volatile components (isobutane and products) under vacuum. The direct relationship between kinematic viscosity and conjunct polymer content is shown in FIG. 5.

The ionic liquid can be any acidic ionic liquid. There can be one or more ionic liquids. The ionic liquid comprises an organic cation and an anion. Suitable cations include, but are not limited to, nitrogen-containing cations and phosphorus-containing cations. Suitable organic cations include, but are not limited to:

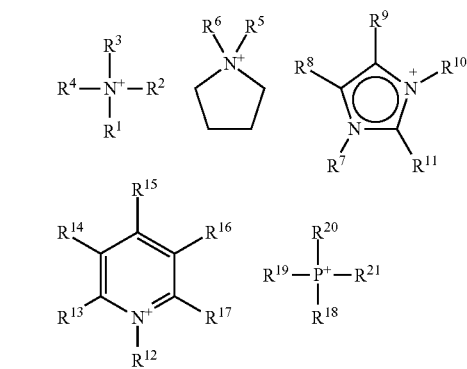

where $R^1$-$R^{21}$ are independently selected from $C_1$-$C_{20}$ hydrocarbons, $C_1$-$C_{20}$ hydrocarbon derivatives, halogens, and H. Suitable hydrocarbons and hydrocarbon derivatives include saturated and unsaturated hydrocarbons, halogen substituted and partially substituted hydrocarbons and mixtures thereof. $C_1$-$C_8$ hydrocarbons are particularly suitable. Lactamium based ionic liquids can also be used including, but not limited to, those described in U.S. Pat. No. 8,709, 236, U.S. application Ser. No. 14/271,308, entitled Synthesis of Lactam Based Ionic Liquids, filed May 6, 2014, and U.S. application Ser. No. 14/271,319, entitled Synthesis of N-Derivatized Lactam Based Ionic Liquids, filed May 6, 2014, which are incorporated by reference.

The anion can be derived from halides, typically halometallates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br^-$. In some embodiments, the metal is aluminum, with the mole fraction of aluminum ranging from 0<Al<0.25 in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2$, $Cu_2Cl_3^-$, $Cu_3Cl_4^-$, $ZnCl_3^-$, $FeCl_3$, $FeCl_4^-$, $Fe_3Cl_7^-$, $PF_6^-$, and $BF_4^-$.

Alkylation

The alkylation reaction using ionic liquid is carried out at mild temperatures, and is typically a two-phase reaction. In some embodiments, cooling may be needed. If cooling is needed, it can be provided using any known methods. The catalyst effects the alkylation of the paraffin and the olefin.

Typical alkylation reaction conditions include a temperature in the range of about −20° C. to the decomposition temperature of the ionic liquid, or about −20° C. to about 100° C., or about −20° C. to about 80° C., or about 0° C. to about 80° C., or about 20° C. to about 80° C. It is preferred to have an ionic liquid that maintains its liquid state through the operating temperature range.

The pressure is typically in the range of atmospheric (0.1 MPa(g)) to about 8.0 MPa(g), or about 0.3 MPa(g) to about 2.5 MPa(g). The pressure is preferably sufficient to keep the reactants in the liquid phase.

The residence time of the reactants in the reaction zone is in the range of a few seconds to hours, or about 0.5 min to about 60 min, or about 1 min to about 60 min, or about 3 min to about 60 min.

The acidity needs to be controlled to provide for suitable alkylation conditions. This can be done with an acid or acid precursor, such as HCl, 2-chlorobutane, or tert-butyl chloride, for example. Alternatively, the excess acid could be stripped from the fresh ionic liquid with, for example, isobutane, nitrogen, or triethylsilane (TES), and the acid level could be controlled at the low level needed during the reaction. Another alternative is to reduce the pressure and add heat to remove the excess acid.

The paraffin and olefin can be introduced separately or as a mixture. The molar ratio between the paraffin and the olefin is in the range between 100:1 and 1:1, or 50:1 and 2:1, or 20:1 and 2:1.

The heat generated by the reaction can be eliminated using any of the means known to the skilled person.

At the reactor outlet, the hydrocarbon phase is separated from the ionic liquid phase by gravity settling based on density differences, or by other separation techniques known to those skilled in the art. The hydrocarbons are separated by distillation, and the unreacted isoparaffin which has not been converted is recycled to the reactor.

Typical alkylation conditions may include a catalyst volume in the reactor of from 1 vol % to 50 vol %, a temperature of from 0° C. to 100° C., a pressure of from 300 kPa to 2500 kPa, an isobutane to olefin molar ratio of from 2 to 20 and a residence time of 1 min to 1 hour.

The paraffin used in the alkylation process preferably comprises a paraffin having from 4 to 10 carbon atoms, or 4 to 8 carbon atoms, or 4 to 5 carbon atoms. The olefin used in the alkylation process preferably has from 2 to 10 carbon atoms, 3 to 8 carbon atoms, or 3 to 5 carbon atoms. One application of the process is to upgrade low value $C_4$ hydrocarbons to higher value alkylates.

To that extent, one specific embodiment is the alkylation of butanes with butylenes to generate $C_8$ compounds. Preferred products include trimethylpentane (TMP), and while other $C_8$ isomers are produced, one competing isomer is dimethylhexane (DMH). The quality of the product stream can be measured in the ratio of TMP to DMH, with a high ratio desired.

In another embodiment, the invention comprises passing an isoparaffin and an olefin to an alkylation reactor, where the alkylation reactor includes an ionic liquid catalyst to react the olefin with the isoparaffin to generate an alkylate. The isoparaffin has from 4 to 10 carbon atoms, and the olefin has from 2 to 10 carbon atoms.

Oligomerization

Oligomerization reaction zones in general are maintained at conditions that may vary widely. Suitable hydrocarbon feed for oligomerization reactions includes $C_2$ to $C_{23}$ olefins. The temperature of the oligomerization reaction zones of the present invention in which an ionic liquid catalyst is used is typically about −20° C. to about 250° C., or 50° C. to about 200° C., or 50° C. to about 150° C. Pressures in the oligomerization zone using the ionic liquid catalyst will be sufficient to maintain the liquid phase in and out of the reactor, typically about 0.3 MPa(g) to about 6.9 MPa(g) (50 to 1000 psig), or about 0.3 MPa(g) to about 3.4 MPa(g) (50 to 500 psig), or about 1.4 MPa(g) to about 2.4 MPa(g) (200 to 350 psig), or about 2.4 MPa(g) to about 6.9 MPa(g) (350 to 1000 psig). Oligomerization conditions may also include a liquid hourly space velocity (LHSV) of about 0.5 to about 50 $hr^{-1}$, or about 1 to about 6 $hr^{-1}$.

Isomerization

Suitable hydrocarbon feed for isomerization reactions includes $C_4$ to $C_{23}$ paraffins.

Suitable reaction conditions include a temperature up to the decomposition temperature of the ionic liquid, typically of about 200° C. or less, or about 175° C. or less, or about 150° C. or less, or about 125° C. or less, or about 100° C. or less, or about 90° C. or less, or about 80° C. or less, or about 70° C. or less, or about 60° C. or less, or in the range of about 0° C. to about 200° C., or about 0° C. to about 175° C., or about 0° C. to about 150° C., or about 10° C. to about 150° C., or about 25° C. to about 150° C., or about 30° C. to about 150° C., or about 40° C. to about 150° C., or about 50° C. to about 150° C., or about 55° C. to about 150° C.

The pressure in the reaction zone is typically in the range of about 0 MPa(g) to about 13.8 MPa(g), or about 0 MPa(g) to about 8.1 MPa(g), or about 0 MPa(g) to about 5 MPa(g), or about 0 MPa(g) to about 3.5 MPa(g). The pressure should be sufficient to ensure that the reaction product is in a liquid state. Small amounts of vapor may also be present, but this should be minimized.

The reaction can take place in the presence of a gas. Suitable gases include, but are not limited to methane, ethane, propane, hydrogen, hydrogen chloride, nitrogen and the like.

The reaction can take place in the presence of an added acid or acid precursor. Suitable acids or acid precursors include, but are not limited to, HCl, 2-chlorobutane, or tert-butyl chloride, for example.

The residence time in the reaction zone is generally less than about 12 hr, or less than about 10 hr, or less than 7 hr, or less than 5 hr, or less than 4 hr, or less than 3 hr, or less than 2 hr, or less than 1 hr. The reaction time can be selected so that a predetermined conversion can be obtained. The reaction time is a function of the degree of mixing, the reaction temperature, the concentration of acid and the mass/volume ratio of liquid catalyst to hydrocarbon being reacted. Generally, increasing any of these conditions will increase the reaction rate.

Isomerization processes utilizing ionic liquid catalysts were described in U.S. Pat. Nos. 9,096,485, 9,102,578, and 9,126,881, each of which is incorporated herein by reference.

Disproportionation

Suitable hydrocarbon feeds for disproportionation reactions include $C_2$ to $C_{23}$ paraffins. Feeds comprising two or more paraffins are also acceptable.

Suitable reaction conditions include a temperature of about less than the decomposition temperature of the ionic liquid, or about 250° C. or less, or about 200° C. or less, or about 175° C. or less, or about 150° C. or less, or about 125° C. or less, or about 100° C. or less, or about 90° C. or less, or about 80° C. or less, or about 70° C. or less, or about 60° C. or less, or in the range of about 0° C. to about 200° C., or about 0° C. to about 175° C., or about 0° C. to about 150° C., or about 10° C. to about 150° C., or about 25° C. to about 150° C., or about 30° C. to about 150° C., or about 40° C. to about 150° C., or about 50° C. to about 150° C., or about 55° C. to about 150° C.

The pressure in the reaction zone is typically in the range of about 0 MPa to about 20.7 MPa, or about 0 MPa to about 8.1 MPa, or about 0 MPa to about 5 MPa, or about 0 MPa to about 3.5 MPa. The pressure should be sufficient to ensure that the reaction product is in a liquid state. Small amounts of vapor may also be present, but this should be minimized.

The reaction can take place in the presence of a gas. Suitable gases include, but are not limited to methane, ethane, propane, hydrogen, hydrogen chloride, nitrogen and the like.

The reaction can take place in the presence of an added acid or acid precursor. Suitable acids or acid precursors include, but are not limited to, HCl, 2-chlorobutane, or tert-butyl chloride, for example. The residence time in the reaction zone is generally less than about 12 hr, or less than about 10 hr, or less than 7 hr, or less than 5 hr, or less than 4 hr, or less than 3 hr, or less than 2 hr, or less than 1 hr. The reaction time can be selected so that a predetermined conversion can be obtained. The reaction time is a function of the degree of mixing, the reaction temperature, the concentration of acid and the mass or volume ratio of liquid catalyst to hydrocarbon being reacted. Generally, increasing any of these conditions will increase the reaction rate.

Disproportionation processes using ionic liquids were described in U.S. Pat. Nos. 9,096,480, 9,096,481, and 9,102,577, each of which is incorporated herein by reference.

Reverse Disproportionation

The microscopic reverse of pentane disproportionation is the combination of one mole of hexane and one mole of butane to form two moles of pentane. This type of reaction is referred to herein as reverse disproportionation. Reverse disproportionation-type reactions can occur in which two paraffins having different carbon numbers react to form two different paraffins having different carbon numbers from those of the feed where the total number of moles of product and moles of carbon and hydrogen in the products does not change from the total number in the feed (e.g., pentane and octane reacting to form hexane and heptane). Utilizing the equilibrium among the various species, the concentration of the product can be controlled by varying the relative ratios of the species. Consequently, two different paraffinic feed sources of varying carbon count can be reacted to obtain a product containing paraffins of intermediate carbon count.

More generally, this process involves the net transfer of $CH_2$ units between paraffins, where $CH_2$ unit refers to the transfer of 1 C and 2 H, not necessarily a methylene unit. The products result from the donation and acceptance of net $CH_2$ units to and from various paraffins. Thus, two paraffinic feeds having different carbon counts can be reacted to produce a product having an intermediate carbon count. For example, the reaction of butane with a larger paraffin, e.g., $C_{16}$, produces a product containing paraffins in the $C_5$ to $C_{15}$ range.

In addition to the net $CH_2$ transfer, the process favors the formation of branched paraffins, which are more valuable than normal paraffins because they have more desirable octane numbers and cloud points.

Typically, hydrocarbons having a carbon number from 1-200 or more can be selected as feeds for the process. Depending on the desired product, one or two (or more) hydrocarbon feeds could be selected.

In some embodiments involving reverse disproportion, one larger and one smaller paraffin feed can be used to produce a product composition having an intermediate carbon count. The smaller feed typically has carbon numbers ranging from 1-198, and the larger feed typically has carbon numbers ranging from 3-200. There is generally a difference of at least 2 or more carbon numbers between the two feeds, or at least 3, or at least 4, or at least 5, or at least 6 or more. In some embodiments involving reverse disproportionation, the reaction mixture has an amount of at least one of the intermediate products equal to or in excess of the amount formed by the disproportionation reaction of either feed alone.

In some embodiments, the smaller feed typically has carbon numbers ranging from 4-23, and the larger feed typically has carbon numbers ranging from 6-25. There is generally a difference of at least 2 or more carbon numbers between the two feeds, or at least 3, or at least 4, or at least 5, or at least 6 or more.

The liquid hydrocarbon feed is contacted with the liquid catalyst at temperatures of in the range of about −20° C. to the decomposition temperature of the ionic liquid, or about 250° C. or less, or about 200° C. or less, or about 175° C. or less, or about 150° C. or less, or about 125° C. or less, or about 100° C. or less, or about 90° C. or less, or about 80° C. or less, or about 70° C. or less, or about 60° C. or less, or in the range of about 0° C. to about 200° C., or about 0° C. to about 175° C., or about 0° C. to about 150° C., or about 10° C. to about 150° C., or about 25° C. to about 150° C., or about 30° C. to about 150° C., or about 40° C. to about 150° C., or about 50° C. to about 150° C., or about 55° C. to about 150° C.

The pressure in the reaction zone is typically in the range of about 0 MPa to about 20.7 MPa, or about 0 MPa to about 8.1 MPa. In some embodiments, the pressure should be sufficient to ensure that the hydrocarbon feed is in a liquid state. Small amounts of vapor may also be present, but this should be minimized. In other embodiments, using propane and other light paraffins, the temperatures may not allow for a liquid state. In this case, a gas phase or a supercritical phase can be used. The reaction typically takes places in the presence of a gas. Suitable gases include, but are not limited to nitrogen, hydrogen, argon, helium, hydrogen chloride and the like.

The reaction can take place in the presence of an added acid or acid precursor. Suitable acids or acid precursors include, but are not limited to, HCl, 2-chlorobutane, or tert-butyl chloride, for example.

The residence time in the reaction zone is generally less than about 10 hr, or less than 7 hr, or less than 5 hr, or less than 4 hr, or less than 3 hr, or less than 2 hr, or less than 1 hr. The reaction time is a function of the degree of mixing, the reaction temperature, the concentration of acid and the mass/volume ratio of liquid catalyst to hydrocarbon being reacted. Generally, increasing any of these conditions will increase the reaction rate.

Reverse disproportionation processes using ionic liquids were described in U.S. Pat. No. 9,096,482, which is incorporated herein by reference.

By the term "about," we mean within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

Specific Embodiments

While the following is described in conjunction with specific embodiments, it will be understood that this description is intended to illustrate and not limit the scope of the preceding description and the appended claims.

A first embodiment of the invention is a method of controlling a hydrocarbon conversion process comprising introducing a reactant into a reaction zone containing an ionic liquid catalyst comprising ionic liquid droplets, the reaction zone having at least two zones, the first zone having a first mass transfer resistance in the ionic liquid droplets and the second zone having a second mass transfer resistance in the ionic liquid droplets greater than the first mass transfer resistance. An embodiment of the invention is one, any or all of prior embodiments in this paragraph up through the first embodiment in this paragraph wherein the second mass transfer resistance is greater than the first mass transfer resistance by changing the first mass transfer resistance, the second mass transfer resistance, or both. An embodiment of the invention is one, any or all of prior embodiments in this paragraph up through the first embodiment in this paragraph wherein the first mass transfer resistance, the second mass transfer resistance, or both are changed by changing a size of droplets of the ionic liquid in the second zone compared to a size of droplets of the ionic liquid catalyst in the first zone. An embodiment of the invention is one, any or all of prior embodiments in this paragraph up through the first embodiment in this paragraph wherein the size of the droplets of ionic liquid in the second zone is changed by increasing a shear rate of the first zone, decreasing a shear rate of the second zone, or both. An embodiment of the invention is one, any or all of prior embodiments in this paragraph up through the first embodiment in this paragraph wherein the size of the droplets of the ionic liquid in the second zone is greater than the size of the droplets in the second zone. An embodiment of the invention is one, any or all of prior embodiments in this paragraph up through the first embodiment in this paragraph wherein the size of the droplets of the ionic liquid is changed using a static mixer designed to increase the size of the droplets of the ionic liquid in the second zone compared to the size of the droplets of the ionic liquid in the first zone. An embodiment of the invention is one, any or all of prior embodiments in this paragraph up through the first embodiment in this paragraph wherein the first mass transfer resistance, the second mass transfer resistance, or both are changed by changing a viscosity of the ionic liquid catalyst under reactor operating conditions in the first zone, the second zone, or both. An embodiment of the invention is one, any or all of prior embodiments in this paragraph up through the first embodiment in this paragraph wherein the viscosity of the ionic liquid catalyst under reactor operating conditions in the first zone, the second zone, or both is changed by operating the first zone at a higher temperature than the second zone. An embodiment of the invention is one, any or all of prior embodiments in this paragraph up through the first embodiment in this paragraph wherein the viscosity of the ionic liquid catalyst under reactor operating conditions in the first zone, the second zone, or both is changed by using an ionic liquid having a higher viscosity in the second zone. An embodiment of the invention is one, any or all of prior embodiments in this paragraph up through the first embodiment in this paragraph wherein the viscosity of the ionic liquid catalyst under reactor operating conditions in the first zone, the second zone, or both is changed by adding a viscosity reducing additive to the ionic liquid catalyst in the first zone, adding a viscosity increasing additive to the ionic liquid in the second zone, or both. An embodiment of the invention is one, any or all of prior embodiments in this paragraph up through the first embodiment in this paragraph wherein the viscosity of the ionic liquid under reactor operating conditions in the second zone is greater than the viscosity of the ionic liquid under reactor operating conditions in the first zone. An embodiment of the invention is one, any or all of prior embodiments in this paragraph up through the first embodiment in this paragraph wherein the reaction zone comprises at least two reactors, and wherein the first reactor comprises the first zone, and the second reactor comprises the second zone. An embodiment of the invention is one, any or all of prior embodiments in this paragraph up through the first embodiment in this paragraph wherein the at least two reactors comprise at least two continuous stirred tank reactors or at least two plug flow reactors. An embodiment of the invention is one, any or all of prior embodiments in this paragraph up through the first embodiment in this paragraph wherein the first mass transfer resistance is changed by adding fresh ionic liquid catalyst or regenerated ionic liquid catalyst to the first zone, or the second mass transfer resistance is changed by recycling spent ionic liquid catalyst to the second reactor, or both. An embodiment of the invention is one, any or all of prior embodiments in this paragraph up through the first embodiment in this paragraph wherein the second mass transfer resistance is changed by increasing an amount of ionic liquid catalyst in the second zone compared to an amount of ionic liquid catalyst in the first zone. An embodiment of the invention is one, any or all of prior embodiments in this paragraph up through the first embodiment in this paragraph wherein the hydrocarbon conversion process is an alkylation process and where the reactant comprises a paraffin having 3 to 8 carbon atoms and an olefin having 2 to 8 carbon atoms.

A second embodiment of the invention is a method of controlling an alkylation process comprising introducing a paraffin having 3 to 8 carbon atoms and an olefin having 2 to 8 carbon atoms into a reaction zone containing an ionic liquid catalyst comprising ionic liquid droplets, the reaction zone having at least two zones, the first zone having a first mass transfer resistance in the ionic liquid droplets and the second zone having a second mass transfer resistance in the ionic liquid droplets greater than the first mass transfer resistance, wherein the second mass transfer resistance is greater than the first mass transfer resistance by changing the first mass transfer resistance, the second mass transfer resistance, or both. An embodiment of the invention is one, any or all of prior embodiments in this paragraph up through the second embodiment in this paragraph wherein the first mass transfer resistance, the second mass transfer resistance, or both are changed by changing a size of droplets of the ionic liquid in the second zone compared to a size of droplets of the ionic liquid catalyst in the first zone. An embodiment of the invention is one, any or all of prior embodiments in this paragraph up through the second embodiment in this paragraph wherein the size of the droplets of ionic liquid in the second zone is changed by: increasing a shear rate of the first zone, decreasing a shear rate of the second zone, or both; or wherein the size of the droplets of the ionic liquid is changed using a static mixer designed to increase the size of the droplets of the ionic liquid in the second zone compared to the size of the droplets of the ionic liquid in the first zone; or both. An embodiment of the invention is one, any or all of prior embodiments in this paragraph up through the second embodiment in this paragraph wherein the first mass transfer resistance, the second mass transfer resistance, or both are changed by at least one of: changing a viscosity of the ionic liquid catalyst under reactor operating conditions in the first zone, the second zone, or both; increasing a temperature of the first zone, decreasing the temperature of the second zone, or both; using a higher viscosity ionic liquid in the second zone; adding a viscosity reducing additive to the ionic liquid catalyst in the first zone, adding a viscosity increasing additive to the ionic liquid in the second zone, or both; and adding fresh ionic liquid catalyst or regenerated ionic liquid catalyst to the first zone, or recycling spent ionic liquid catalyst to the second reactor, or both.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A method of minimizing secondary reactions producing undesired products in an alkylation reaction of a paraffin and an olefin comprising:
   introducing a paraffin having 3 to 8 carbon atoms and an olefin having 2 to 8 carbon atoms into an alkylation reactor containing an ionic liquid catalyst comprising ionic liquid droplets to alkylate the paraffin with the olefin to produce an alkylated product, the reaction reactor having at least two reaction zones with the second reaction zone down-stream from the first reaction zone, the first reaction zone having a first mass transfer resistance in the ionic liquid droplets and the second reaction zone having a second mass transfer resistance in the ionic liquid droplets greater than the first mass transfer resistance, wherein the second mass transfer resistance is greater than the first mass transfer resistance by changing the first mass transfer resistance, the second mass transfer resistance, or both; wherein the first mass transfer resistance, the second mass transfer resistance, or both are changed by at least one of:
   by changing a size of droplets of the ionic liquid catalyst;
   by changing a viscosity of the ionic liquid catalyst; and
   by adjusting fresh/regenerated ionic liquid catalyst to reaction zones.

2. The method of claim 1 wherein the first mass transfer resistance, the second mass transfer resistance, or both are changed by changing a size of droplets of the ionic liquid in the second zone compared to a size of droplets of the ionic liquid catalyst in the first zone.

3. The method of claim 2 wherein the size of the droplets of ionic liquid in the second zone is changed by increasing a shear rate of the first zone, decreasing a shear rate of the second zone, or both.

4. The method of claim 2 wherein the size of the droplets of the ionic liquid in the second zone is greater than the size of the droplets in the second zone.

5. The method of claim 2 wherein the size of the droplets of the ionic liquid is changed using a static mixer designed to increase the size of the droplets of the ionic liquid in the second zone compared to the size of the droplets of the ionic liquid in the first zone.

6. The method of claim 1 wherein the first mass transfer resistance, the second mass transfer resistance, or both are changed by changing a viscosity of the ionic liquid catalyst under reactor operating conditions in the first zone, the second zone, or both.

7. The method of claim 6 wherein the viscosity of the ionic liquid catalyst under reactor operating conditions in the first zone, the second zone, or both is changed by operating the first zone at a higher temperature than the second zone.

8. The method of claim 6 wherein the viscosity of the ionic liquid catalyst under reactor operating conditions in the first zone, the second zone, or both is changed by using an ionic liquid having a higher viscosity in the second zone.

9. The method of claim 6 wherein the viscosity of the ionic liquid catalyst under reactor operating conditions in the first zone, the second zone, or both is changed by adding a viscosity reducing additive to the ionic liquid catalyst in the first zone, adding a viscosity increasing additive to the ionic liquid in the second zone, or both.

10. The method of claim 6 wherein the viscosity of the ionic liquid under reactor operating conditions in the second zone is greater than the viscosity of the ionic liquid under reactor operating conditions in the first zone.

11. The method of claim 1 wherein the reaction zone comprises at least two reactors, and wherein the first reactor comprises the first zone, and the second reactor comprises the second zone.

12. The method of claim 11 wherein the reaction zone comprises at least two continuous stirred tank reactors or at least two plug flow reactors.

13. The method of claim 11 wherein the first mass transfer resistance is changed by adding fresh ionic liquid catalyst or regenerated ionic liquid catalyst to the first zone, or the second mass transfer resistance is changed by recycling spent ionic liquid catalyst to the second reactor, or both.

14. The method of claim 1 wherein the second mass transfer resistance is changed by increasing an amount of ionic liquid catalyst in the second zone compared to an amount of ionic liquid catalyst in the first zone.

* * * * *